(12) United States Patent
Kim et al.

(10) Patent No.: US 12,215,063 B2
(45) Date of Patent: Feb. 4, 2025

(54) METHOD FOR PREPARING DEUTERATED COMPOUND

(71) Applicant: LG CHEM, LTD., Seoul (KR)

(72) Inventors: Sunmin Kim, Daejeon (KR); Wanpyo Hong, Daejeon (KR); Woochul Lee, Daejeon (KR); Kyung Seok Jeong, Daejeon (KR); Woo Han Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 181 days.

(21) Appl. No.: 17/913,758

(22) PCT Filed: Mar. 23, 2021

(86) PCT No.: PCT/KR2021/003562
§ 371 (c)(1),
(2) Date: Sep. 22, 2022

(87) PCT Pub. No.: WO2021/210800
PCT Pub. Date: Oct. 21, 2021

(65) Prior Publication Data
US 2023/0331639 A1    Oct. 19, 2023

(30) Foreign Application Priority Data

Apr. 17, 2020    (KR) ................ 10-2020-0046870

(51) Int. Cl.
| | | |
|---|---|---|
| *C07B 59/00* | (2006.01) | |
| *C07C 1/32* | (2006.01) | |
| *C07C 15/28* | (2006.01) | |

(52) U.S. Cl.
CPC ........ *C07B 59/001* (2013.01); *C07B 2200/05* (2013.01)

(58) Field of Classification Search
CPC ..... C07B 59/001; C07B 2200/05; C07C 1/32; C07C 1/322; C07C 15/28
See application file for complete search history.

(56) References Cited

U.S. PATENT DOCUMENTS

| | | |
|---|---|---|
| 2011/0095273 A1 | 4/2011 | Meng et al. |
| 2011/0133632 A1* | 6/2011 | Lecloux ............... C07D 209/86 |
| | | 252/301.16 |

FOREIGN PATENT DOCUMENTS

| | | |
|---|---|---|
| CN | 102639671 | 8/2012 |
| CN | 108779072 | 11/2018 |

(Continued)

OTHER PUBLICATIONS

Zimmermann, "Specifically deuteriated intermediates for the synthesis of liquid crystals and liquid-crystalline polymers," Liquid Crystals, 1989, vol. 4, No. 6, 591-618.

(Continued)

*Primary Examiner* — In Suk C Bullock
*Assistant Examiner* — Jason Y Chong
(74) *Attorney, Agent, or Firm* — Bryan Cave Leighton Paisner LLP

(57) ABSTRACT

A method for preparing a deuterated compound, and a composition including the deuterated compound are provided. The method comprises preparing a compound of Chemical Formula 2 by reacting a compound of Chemical Formula 1; a deuterium source; and a metal catalyst, and forming a compound of Chemical Formula 3 by using the compound of Chemical Formula 2:

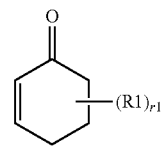

[Chemical Formula 1]

[Chemical Formula 2]

(Continued)

-continued

[Chemical Formula 3]

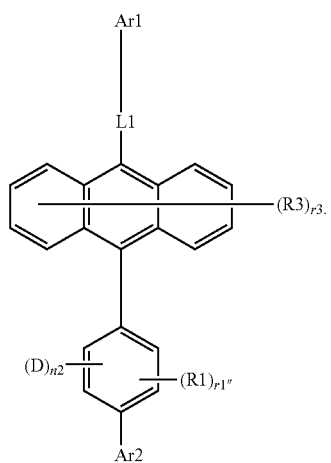

(56) References Cited

FOREIGN PATENT DOCUMENTS

| | | | |
|---|---|---|---|
| JP | 2005-248027 | A | 9/2005 |
| JP | 2009-137911 | A | 6/2009 |
| JP | 2014-111561 | A | 6/2019 |
| KR | 10-2012-0026095 | A | 3/2012 |
| KR | 10-2012-0112520 | A | 10/2012 |
| KR | 10-1978650 | B1 | 5/2019 |
| KR | 10-1978651 | B1 | 5/2019 |

OTHER PUBLICATIONS

Chinese Master's Theses Full-text Data base Engineering Science and Technology I, China Academic Journal, Apr. 2019.

8 Claims, 5 Drawing Sheets

\* cited by examiner

METHOD FOR PREPARING DEUTERATED COMPOUND

CROSS-REFERENCE TO RELATED APPLICATION

This application is a National Stage Application of International Application No. PCT/KR2021/003562 filed on Mar. 23, 2021, which claims priority to and the benefits of Korean Patent Application No. 10-2020-0046870 filed on Apr. 17, 2020, the disclosures of which are incorporated herein by reference in their entirety.

FIELD OF DISCLOSURE

The present specification relates to a method for preparing a deuterated compound.

BACKGROUND

Deuterium, an isotope of hydrogen, has a natural abundance of approximately 0.015%. Deuterated compounds having a high degree of deuteration are well known.

As methods of deuteration, a method of treating an undeuterated compound with a material such as $D_2SO_4$ or $D_3PO_4 \cdot BF_3/D_2O$ over a period of hours or days, a method of treating an undeuterated compound with a deuterated solvent under the presence of a Lewis acid H/D exchange catalyst such as aluminum trichloride or ethyl aluminum chloride, a method of treating an undeuterated compound with an acid or base-catalyst under a high temperature and high pressure condition, and the like, are known.

An improved method for forming a deuterated aromatic compound with an excellent deuterium conversion rate has been required.

RELATED ART (Patent Document 1) JP 2005-248027 A

SUMMARY

The present specification is directed to providing a method for preparing a deuterated compound. Specifically, the present specification is directed to providing a method for preparing a deuterated compound having an excellent deuterium conversion rate of a phenyl group linked to anthracene, and using a small amount of deuterium source.

One embodiment of the present specification provides a method for preparing a deuterated compound, the method including Step 1 of preparing a compound of Chemical Formula 2 by reacting a compound of Chemical Formula 1; a deuterium source; and a metal catalyst, and Step 2 of forming a compound of Chemical Formula 3 using the compound of Chemical Formula 2.

[Chemical Formula 1]

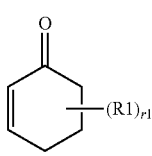

[Chemical Formula 2]

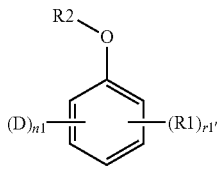

[Chemical Formula 3]

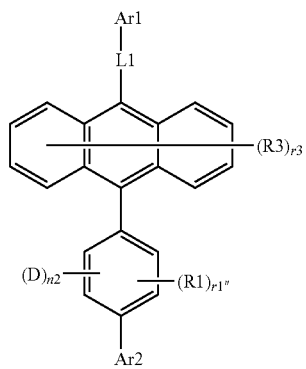

In Chemical Formulae 1 to 3,

R1 is hydrogen; a cyano group; a nitro group; a halogen group; a hydroxyl group; a substituted or unsubstituted alkyl group; a substituted or unsubstituted cycloalkyl group; a substituted or unsubstituted aryl group; or a substituted or unsubstituted heteroaryl group, R2 is hydrogen or deuterium, R3 is hydrogen; deuterium; a substituted or unsubstituted alkyl group; a substituted or unsubstituted cycloalkyl group; a substituted or unsubstituted aryl group; or a substituted or unsubstituted heteroaryl group, Ar1 and Ar2 are the same as or different from each other, and each independently a substituted or unsubstituted aryl group; or a substituted or unsubstituted heteroaryl group, L1 is a direct bond; a substituted or unsubstituted arylene group; or a substituted or unsubstituted heteroarylene group, D is deuterium, r1 is an integer of 0 to 8, r1' is an integer of 0 to 4, r1" is an integer of 0 to 3, and when r1, r1' and r1" are 2 or greater, R1s are the same as or different from each other, r3 is an integer of 0 to 8, and when r3 is 2 or greater, R3s are the same as or different from each other, and n1 is an integer of 1 to 5, and n2 is an integer of 1 to 4.

Another embodiment of the present specification provides a composition including Compound H1 of Chemical Formula 3 having n2 of 4; and Compound H2 of Chemical Formula 3 having n2 of 2 or less, wherein a mass ratio of Compound H1 to Compound H2 is 7:3 to 99.9:0.1.

[Chemical Formula 3]

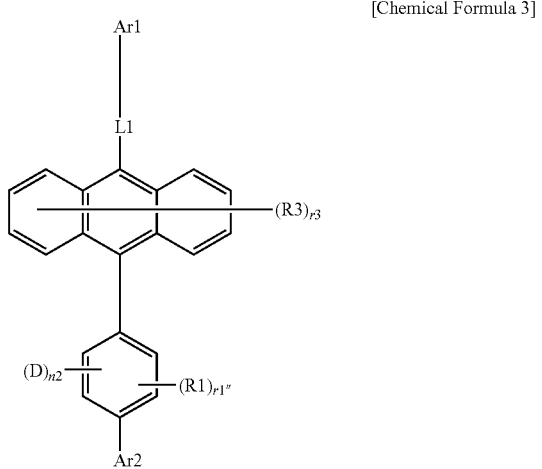

In Chemical Formula 3,
R1 is hydrogen; a cyano group; a nitro group; a halogen group; a hydroxyl group; a substituted or unsubstituted alkyl group; a substituted or unsubstituted cycloalkyl group; a substituted or unsubstituted aryl group; or a substituted or unsubstituted heteroaryl group,
R3 is hydrogen; deuterium; a substituted or unsubstituted alkyl group; a substituted or unsubstituted cycloalkyl group; a substituted or unsubstituted aryl group; or a substituted or unsubstituted heteroaryl group,
Ar1 and Ar2 are the same as or different from each other, and each independently a substituted or unsubstituted aryl group; or a substituted or unsubstituted heteroaryl group,
L1 is a direct bond; a substituted or unsubstituted arylene group; or a substituted or unsubstituted heteroarylene group,
D is deuterium,
r1″ is an integer of 0 to 3, and when r1″ is 2 or greater, R1s are the same as or different from each other,
r3 is an integer of 0 to 8, and when r3 is 2 or greater, R3s are the same as or different from each other, and
n2 is an integer of 1 to 4.
Herein, Ar1, L1, R3, r3 and Ar2 of Compounds H1 and H2 are the same as each other. In other words, all the substituents other than n2, R1 and r1″ are the same.

A method for preparing a deuterated compound according to one embodiment of the present specification is capable of reducing an amount of deuterium source used, and increasing a deuterium substitution rate of a phenyl group positioned between anthracene and a substituent.

When using a deuterated compound prepared using the preparation method in an organic light emitting device, long lifetime properties of the device increase.

DETAILED DESCRIPTION

Figure 1:
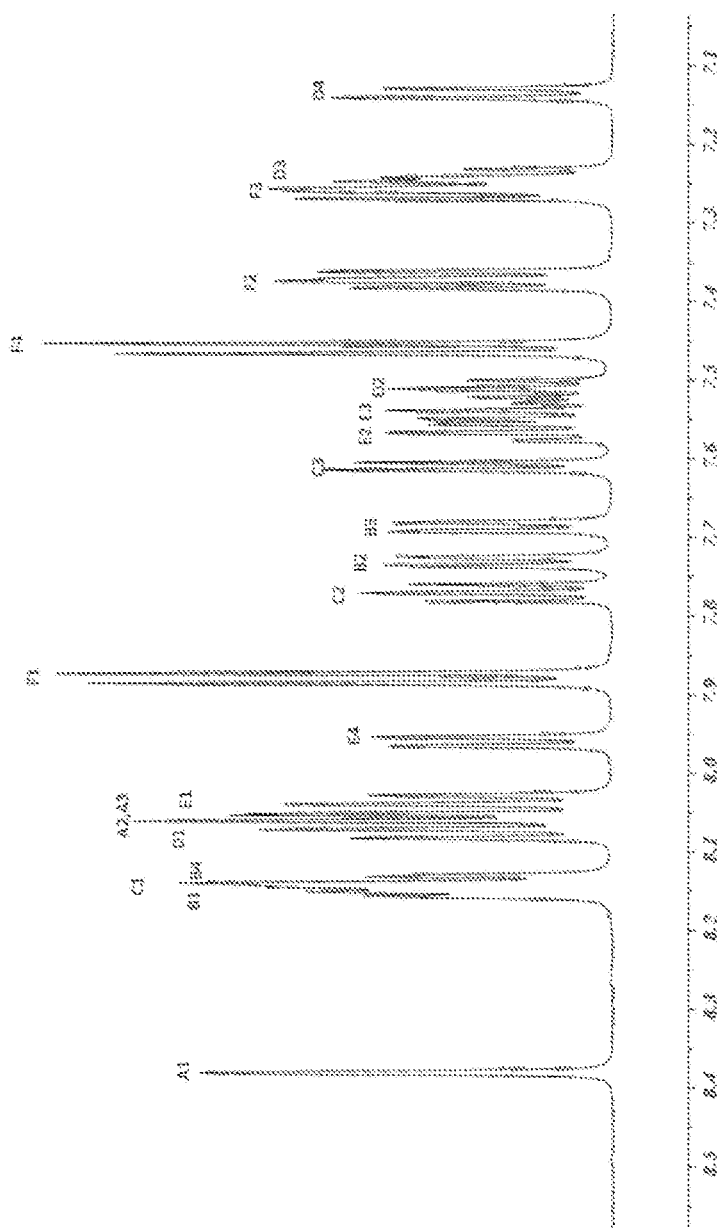
FIG. 1 is an NMR spectrum of 9-(naphthalen-1-yl)-10-(4-(naphthalen-2-yl)phenyl)anthracene not substituted with deuterium.

Hereinafter, the present specification will be described in more detail.

As a deuteration method, a method of deuterating an undeuterated compound by treating with a deuterated solvent is known. With such a reaction, hydrogen at a sterically unfree site is difficult to be deuterated. When the following undeuterated 9-(naphthalen-1-yl)-10-(4-(naphthalen-2-yl)phenyl)anthracene goes through a deuterium exchange reaction, hydrogen of the phenyl group positioned between the anthracene and the naphthyl, specifically, the position close to the anthracene is not sterically free, and the deuterium exchange reaction is difficult to occur. In addition, such a method requires an over-equivalent of deuterium source (for example, 200 eq. or greater) in order to increase a deuterium substitution rate.

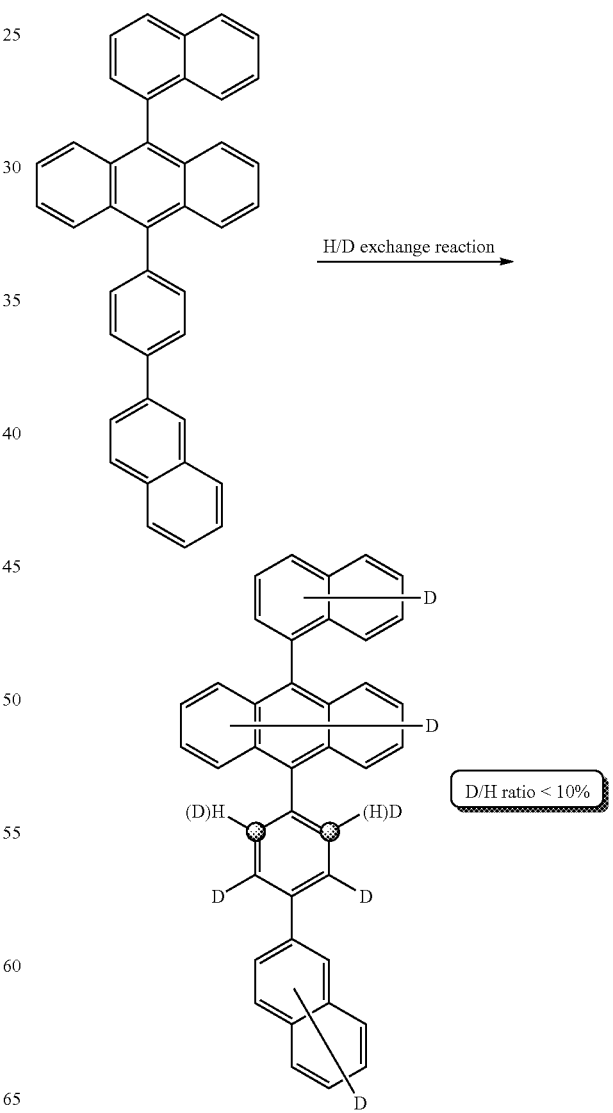

A deuterated intermediate may be used to increase a deuterium substitution rate of the phenyl group positioned between the anthracene and the substituent. The present disclosure provides a method for preparing a deuterated compound using a deuterated intermediate. The present disclosure is capable of increasing a deuterium substitution rate of the phenyl group and reducing an amount of deuterium source used.

In the present specification, "deuterated" means available hydrogens of a compound being substituted with deuterium.

In the present specification, "perdeuterated" means all hydrogens being substituted with deuterium.

In the present specification, being substituted with deuterium by N % means N % of available hydrogens in the corresponding structure being substituted with deuterium. For example, being substituted with deuterium by 25% in dibenzofuran means two of eight hydrogens in dibenzofuran being substituted with deuterium.

In the present specification, a "degree of deuteration" or "deuterium substitution rate" may be identified using known methods such as nuclear magnetic resonance (1H NMR), TLC/MS (thin-layer chromatography/mass spectrometry) or GC/MS (gas chromatography/mass spectrometry).

Specifically, when analyzing a "degree of deuteration" or "deuterium substitution rate" using nuclear magnetic resonance (1H NMR), the degree of deuteration or deuterium substitution rate may be calculated from the integrated quantity of total peaks through the integration ratio in 1H NMR after adding dimethylformamide (DMF) as an internal standard.

In addition, when analyzing a "degree of deuteration" or "deuterium substitution rate" through TLC/MS (thin-layer chromatography/mass spectrometry), the substitution rate may be calculated based on the maximum value (median value) of distribution that molecular weights form at the end of the reaction.

In one embodiment of the present specification, the "degree of deuteration" or "deuterium substitution rate" may be analyzed by analyzing NMR under the following condition.

NMR device: Bruker 700 MHz NMR
Select corresponding probe: Probe (PABBO)
D-solvent: (THF-d8)
Experiment temperature: 298K
Parameter set up follows SOP procedure.

In the present specification, a method "including" a certain step means capable of further including other constituting steps, and does not exclude other steps unless particularly stated on the contrary.

In the present specification, Cn means n carbon atoms.

In the present specification, "Cn-Cm" means "n to m carbon atoms".

Examples of substituents in the present specification are described below, however, the substituents are not limited thereto.

The term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

In one embodiment of the present specification, the term "substituted or unsubstituted" means being substituted with one or more substituents selected from the group consisting of deuterium; a C1-C10 alkyl group; a C6-C30 aryl group; and a C2-C30 heteroaryl group or a substituent linking two or more substituents selected from the above-described group, or having no substituents.

In the present specification, examples of the halogen group may include fluorine, chlorine, bromine or iodine.

In the present specification, the alkyl group may be linear or branched, and although not particularly limited thereto, the number of carbon atoms is preferably 1 to 30; 1 to 20; 1 to 10; or 1 to 5. Specific examples thereof may include methyl, ethyl, propyl, n-propyl, isopropyl, butyl, n-butyl, isobutyl, t-butyl, sec-butyl, 1-methylbutyl, 1-ethylbutyl, pentyl, n-pentyl, isopentyl, neopentyl, t-pentyl, hexyl, n-hexyl, 1-methylpentyl, 2-methylpentyl, 3,3-dimethylbutyl, 2-ethylbutyl, heptyl, n-heptyl, 1-methylhexyl, cyclopentylmethyl, cyclohexylmethyl, octyl, n-octyl, t-octyl, 1-methylheptyl, 2-ethylhexyl, 2-propylpentyl, n-nonyl, 2,2-dimethylheptyl, 1-ethylpropyl, 1,1-dimethylpropyl, isohexyl, 4-methylhexyl, 5-methylhexyl and the like, but are not limited thereto.

In the present specification, the aryl group means monovalent aromatic hydrocarbon or a monovalent group of an aromatic hydrocarbon derivative. In the present specification, the aromatic hydrocarbon means a compound including a ring having pi electrons completely conjugated and planar, and the group derived from the aromatic hydrocarbon means a structure in which aromatic hydrocarbon or cyclic aliphatic hydrocarbon is fused to the aromatic hydrocarbon. In addition, in the present specification, the aryl group includes a monovalent group in which two or more aromatic hydrocarbons or aromatic hydrocarbon derivatives are linked to each other. The aryl group is not particularly limited, but preferably has 6 to 50; 6 to 30; 6 to 25; 6 to 20; 6 to 18; or 6 to 13 carbon atoms, and the aryl group may be monocyclic or polycyclic. Specific examples of the monocyclic aryl group may include a phenyl group, a biphenyl group, a terphenyl group and the like, but are not limited thereto. Specific examples of the polycyclic aryl group may include a naphthyl group, an anthracenyl group, a phenanthryl group, a triphenyl group, a pyrenyl group, a perylenyl group, a chrysenyl group, a fluorenyl group and the like, but are not limited thereto.

In the present specification, the heterocyclic group includes one or more atoms that are not carbon, that is, heteroatoms, and specifically, the heteroatom may include one or more atoms selected from the group consisting of O, N, S and the like. Although not particularly limited thereto, the number of carbon atoms is preferably 2 to 50; 2 to 30; 2 to 20; 2 to 18; or 2 to 13, and the heterocyclic group may be monocyclic or polycyclic. Examples of the heterocyclic group may include a thiophene group, a furanyl group, a pyrrole group, an imidazole group, a thiazole group, an oxazole group, an oxadiazole group, a pyridine group, a bipyridine group, a pyrimidine group, a triazine group, a triazole group, an acridine group, a pyridazine group, a pyrazine group, a quinoline group, a quinazoline group, a quinoxaline group, a phthalazine group, a pyridopyrimidine group, a pyridopyrazine group, a pyrazinopyrazine group, an isoquinoline group, an indole group, a carbazole group, a benzoxazole group, a benzimidazole group, a benzothiazole group, a benzocarbazole group, a benzothiophene group, a dibenzothiophene group, a benzofuran group, a phenanthroline group, a thiazole group, an isoxazole group, an oxadiazole group, a thiadiazole group, a benzothiazole group, a phenothiazine group, a dibenzofuran group, a dihydrophenothiazine group, a dihydrobenzoisoquinoline group, a chromene group and the like, but are not limited thereto.

In the present specification, the heteroaryl group means a monovalent aromatic heteroring. Herein, the aromatic heteroring means a monovalent group of an aromatic ring or aromatic ring derivative, and means a group including one or more of N, O and S in the ring as a heteroatom. The aromatic ring derivative includes all structures in which an aromatic ring or an aliphatic ring is fused to the aromatic ring. In addition, in the present specification, the heteroaryl group includes a monovalent group in which two or more heteroatom-including aromatic rings or heteroatom-including aromatic ring derivatives are linked to each other. The heteroaryl group preferably has 2 to 50; 2 to 30; 2 to 20; 2 to 18; or 2 to 13 carbon atoms.

In the present specification, the arylene group means the aryl group having two bonding sites, that is, a divalent group. The descriptions on the aryl group provided above may be applied thereto except for those that are each a divalent group.

In the present specification, the heteroarylene group means the heteroaryl group having two bonding sites, that is, a divalent group. The descriptions on the heteroaryl group provided above may be applied thereto except for those that are each a divalent group.

Hereinafter, the preparation method according to one embodiment of the present disclosure will be described in detail.

A method for preparing a deuterated compound according to one embodiment of the present specification includes Step 1 of preparing a compound of Chemical Formula 2 by reacting a compound of Chemical Formula 1; a deuterium source; and a metal catalyst, and Step 2 of forming a compound of Chemical Formula 3 using the compound of Chemical Formula 2.

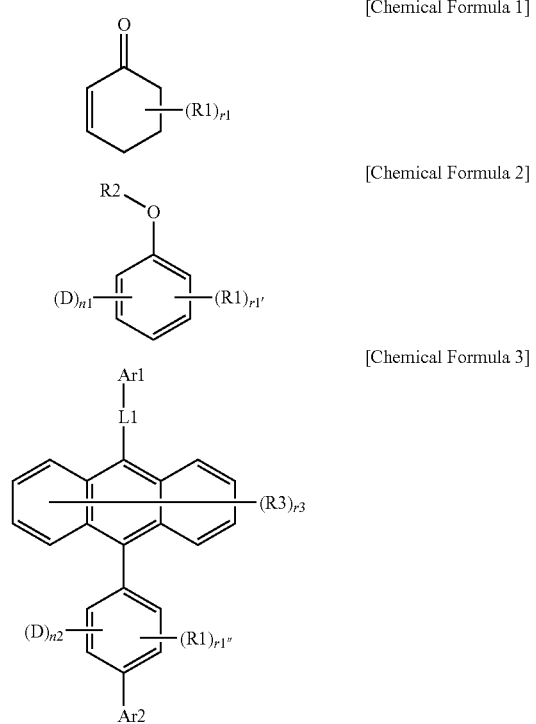

[Chemical Formula 1]

[Chemical Formula 2]

[Chemical Formula 3]

In Chemical Formulae 1 to 3,

R1 is hydrogen; a cyano group; a nitro group; a halogen group; a hydroxyl group; a substituted or unsubstituted alkyl group; a substituted or unsubstituted cycloalkyl group; a substituted or unsubstituted aryl group; or a substituted or unsubstituted heteroaryl group, R2 is hydrogen or deuterium, R3 is hydrogen; deuterium; a substituted or unsubstituted alkyl group; a substituted or unsubstituted cycloalkyl group; a substituted or unsubstituted aryl group; or a substituted or unsubstituted heteroaryl group, Ar1 and Ar2 are the same as or different from each other, and each independently a substituted or unsubstituted aryl group; or a substituted or unsubstituted heteroaryl group, L1 is a direct bond; a substituted or unsubstituted arylene group; or a substituted or unsubstituted heteroarylene group, D is deuterium, r1 is an integer of 0 to 8, r1' is an integer of 0 to 4, r1" is an integer of 0 to 3, and when r1, r1' and r1" are 2 or greater, R1s are the same as or different from each other, r3 is an integer of 0 to 8, and when r3 is 2 or greater, R3s are the same as or different from each other, and n1 is an integer of 1 to 5, and n2 is an integer of 1 to 4.

Through Step 1, the compound of Chemical Formula 2 including a benzene ring (deuterated intermediate) may be obtained. In the produced anthracene compound of Chemical Formula 3, the benzene ring of Chemical Formula 2 becomes a phenylene group positioned between the anthracene and the substituent. The deuterated intermediate prepared in Step 1 has a high deuterium substitution rate, and the amount of deuterium source required in Step 1 is small.

In the present specification, mixing includes not only a stirring reaction in a stirrer, but also leaving in a reactor unattended.

In one embodiment of the present specification, mixing means leaving in a reactor unattended.

In one embodiment of the present specification, n1+r1' is an integer of 0 to 5.

In one embodiment of the present specification, n2+r1" is an integer of 0 to 4.

In one embodiment of the present specification, R1 is hydrogen; a cyano group; a nitro group; a halogen group; a hydroxyl group; a substituted or unsubstituted C1-C10 alkyl group; a substituted or unsubstituted C3-C30 cycloalkyl group; a substituted or unsubstituted C6-C30 aryl group; or a substituted or unsubstituted C2-C30 heteroaryl group.

In one embodiment of the present specification, R1 is hydrogen.

In one embodiment of the present specification, r1 is 0.

In one embodiment of the present specification, R2 is deuterium.

In one embodiment of the present specification, n1 is 4 or 5.

In one embodiment of the present specification, n1 is 5.

In one embodiment of the present specification, the deuterium source includes a perdeuterated solvent.

In one embodiment of the present specification, the deuterium source is one selected from the group consisting of heavy water ($D_2O$), perdeuterated benzene (benzene-$D_6$), perdeuterated toluene (toluene-$D_8$), perdeuterated xylene (xylene-$D_{10}$), deuterium-hydrochloric acid (DCl), deuterium-sulfuric acid ($D_2SO_4$), deuterium-trifluoroacetic acid ($CF_3COOD$), deuterium-triflic acid ($CF_3SO_3OD$), deuterium-chloroform ($CDCl_3$) and perdeuterated methanol ($CD_3OD$), or a mixture of two or more thereof. However, the deuterium source is not limited to the examples.

In one embodiment of the present specification, the deuterium source is one selected from the group consisting of heavy water (D₂O), perdeuterated benzene (benzene-D₆), perdeuterated toluene (toluene-D₈), perdeuterated xylene (xylene-D₁₀), deuterium-hydrochloric acid (DCl), deuterium-sulfuric acid (D₂SO₄), deuterium-trifluoroacetic acid (CF₃COOD), deuterium-triflic acid (CF₃SO₃OD), deuterium-chloroform (CDCl₃) and perdeuterated methanol (CD₃OD).

In one embodiment of the present specification, the deuterium source is heavy water (D₂O) or perdeuterated benzene (benzene-D₆).

In one embodiment of the present specification, the deuterium source functions as a solvent.

In one embodiment of the present specification, the deuterium source used in Step 1 is included in 1 equivalent to 50 equivalents with respect to 1 equivalent of the compound of Chemical Formula 1. The deuterium source is preferably included in 1 equivalent to 25 equivalents, and more preferably in 5 equivalents to 15 equivalents. According to the present disclosure, the deuterium substitution rate may increase while using less deuterium source.

In one embodiment of the present specification, an additional solvent may be included in Step 1. Examples of the solvent may include chlorine-based solvents such as chloroform, methylene chloride, 1,2-dichloroethane, 1,1,2-trichloroethane, chlorobenzene and o-dichlorobenzene; ether-based solvents such as tetrahydrofuran and dioxane; aromatic hydrocarbon-based solvents such as toluene, xylene, trimethylbenzene and mesitylene; aliphatic hydrocarbon-based solvents such as cyclohexane, methylcyclohexane, n-pentane, n-hexane, n-heptane, n-octane, n-nonane and n-decane; ketone-based solvents such as acetone, methyl ethyl ketone and cyclohexanone; ester-based solvents such as ethyl acetate, butyl acetate and ethyl cellosolve acetate; polyalcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin and 1,2-hexanediol, and derivatives thereof; alcohol-based solvents such as methanol, ethanol, propanol, isopropanol and cyclohexanol, and the like, however, the solvent is not limited thereto, and any solvent may be used as long as it is capable of dissolving or dispersing the compound according to one embodiment of the present specification.

In another embodiment, the solvent may be used either alone in one type, or as a mixture of two or more types thereof.

In one embodiment of the present specification, the metal catalyst is platinum, palladium, rhodium, ruthenium, nickel, cobalt, iron, oxides thereof, complexes thereof, or a mixture of two or more thereof. However, the metal catalyst is not limited to the examples described above.

In one embodiment of the present specification, Step 1 specifically includes:
Step 1-1 of stirring a mixture of the compound of Chemical Formula 1 and the deuterium source;
Step 1-2 of mixing the metal catalyst with the mixture and adjusting a temperature; and
Step 1-3 of obtaining the compound of Chemical Formula 2.

In one embodiment of the present specification, Step 1-1 is conducted at room temperature, and Step 1-2 is conducted at a temperature of 80° C. to 120° C.

In the present specification, room temperature means a temperature of 23° C. to 28° C.

In the present specification, normal pressure refers to the same pressure as atmospheric pressure, and means 970 hPa to 1040 hPa.

In one embodiment of the present specification, Step 1 is conducted at a temperature of 20° C. or higher.

In one embodiment of the present specification, Step 1 is conducted at a temperature of 150° C. or lower.

In one embodiment of the present specification, Step 1 is conducted at a temperature of 50° C. to 110° C.

After Step 1, the anthracene compound of Chemical Formula 3 is obtained in Step 2 from the compound of Chemical Formula 2 (deuterated intermediate) through a series of reactions.

Specifically, Step 2 includes:
Step 2-1 of halogenating the compound of Chemical Formula 2 to form a halogenated compound;
Step 2-2 of substituting halogen of the halogenated compound with Ar2 by reacting the halogenated compound with an organic boron compound containing Ar2 to form a compound including Ar2; and
Step 2-3 of reacting the compound including Ar2 and an anthracene derivative to form a carbon-carbon bond therebetween.

In Step 2-1, the compound of Chemical Formula 2 reacts with NBS (N-bromosuccinimide) to attack C—H or C-D having the weakest bonding strength, and thereby to release H or D and link the halogen group. Specifically, the halogen group may be linked at a para position with respect to O of Chemical Formula 2.

In Step 2-2, the halogenated compound and an organic boron compound including Ar2 react to release the halogen group and link Ar2 at the same position. Herein, a carbon-carbon bond such as Suzuki coupling may be used.

Step 2-3 is a step of obtaining the compound of Chemical Formula 3. Specifically, the —OR2 group of the compound including Ar2 is substituted with a halogen group or a leaving group including boron, and then the result reacts with an anthracene derivative to obtain the compound of Chemical Formula 3. Herein, the anthracene derivative means the following structure.

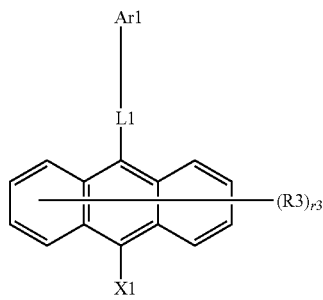

In the structure, Ar1, L1 and R3 have the same definitions as in Chemical Formula 3, and
X1 is a halogen group; or a leaving group including boron.

In the present specification, the leaving group including boron means boronic acid; or a borane derivative.

In one embodiment of the present specification, n2 is 3 or 4.

In one embodiment of the present specification, n2 is 4.

In one embodiment of the present specification, Ar1 and Ar2 are the same as or different from each other, and each independently a substituted or unsubstituted C6-C60 aryl group; or a substituted or unsubstituted C2-C60 heteroaryl group.

In one embodiment of the present specification, Ar1 and Ar2 are the same as or different from each other, and each independently a substituted or unsubstituted C6-C30 aryl group; or a substituted or unsubstituted C2-C30 heteroaryl group.

In one embodiment of the present specification, Ar1 and Ar2 are the same as or different from each other, and each independently a substituted or unsubstituted C6-C20 aryl group; or a substituted or unsubstituted C2-C30 heteroaryl group.

In one embodiment of the present specification, Ar1 and Ar2 are the same as or different from each other, and each independently a substituted or unsubstituted phenyl group; a substituted or unsubstituted biphenyl group; a substituted or unsubstituted terphenyl group; a substituted or unsubstituted naphthyl group; a substituted or unsubstituted phenanthrenyl group; a substituted or unsubstituted anthracenyl group; a substituted or unsubstituted triphenylene group; a substituted or unsubstituted fluoranthenyl group; a substituted or unsubstituted phenalene group; a substituted or unsubstituted fluorenyl group; a substituted or unsubstituted benzofluorenyl group; a substituted or unsubstituted spirobifluorenyl group; a substituted or unsubstituted furan group; a substituted or unsubstituted thiophene group; a substituted or unsubstituted dibenzofuran group; a substituted or unsubstituted dibenzothiophene group; a substituted or unsubstituted naphthobenzofuran group; or a substituted or unsubstituted naphthobenzothiophene group.

In one embodiment of the present specification, Ar1 and Ar2 are the same as or different from each other, and each independently a C6-C30 aryl group unsubstituted or substituted with deuterium, a C1-C10 alkyl group, a C1-C10 alkyl group substituted with deuterium, a C6-C30 aryl group, or a C6-C30 aryl group substituted with deuterium; or a C2-C30 heteroaryl group unsubstituted or substituted with deuterium, a C6-C30 aryl group, or a C6-C30 aryl group substituted with deuterium.

In one embodiment of the present specification, Ar1 and Ar2 are the same as or different from each other, and each independently a phenyl group; a biphenyl group; a 1-naphthyl group; a 2-naphthyl group; a terphenyl group; a phenanthrenyl group; an anthracenyl group; a triphenylene group; a dibenzofuran group; a phenyl-dibenzofuran group; a dibenzothiophene group; a naphthobenzofuran group; a tolyl group; or a xylyl group, and the substituents of Ar1 and Ar2 are unsubstituted or substituted with deuterium.

In one embodiment of the present specification, Ar1 and Ar2 are the same as or different from each other, and each independently a phenyl group; a biphenyl group; a 1-naphthyl group; a 2-naphthyl group; a 1-dibenzofuran group; 2-dibenzofuran group; a 3-dibenzofuran group; or a 4-dibenzofuran group, and the substituents of Ar1 and Ar2 are unsubstituted or substituted with deuterium.

In one embodiment of the present specification, Ar1 and Ar2 are different from each other.

In one embodiment of the present specification, L1 is a direct bond; a substituted or unsubstituted C6-C60 arylene group; or a substituted or unsubstituted C2-C60 heteroarylene group.

In one embodiment of the present specification, L1 is a direct bond; a substituted or unsubstituted C6-C30 arylene group; or a substituted or unsubstituted C2-C30 heteroarylene group.

In one embodiment of the present specification, L1 is a direct bond; a substituted or unsubstituted C6-C20 arylene group; or a substituted or unsubstituted C2-C20 heteroarylene group.

In one embodiment of the present specification, L1 is a direct bond; a substituted or unsubstituted phenylene group; a substituted or unsubstituted biphenylene group; or a substituted or unsubstituted naphthylene group.

In one embodiment of the present specification, L1 is a direct bond; a phenylene group unsubstituted or substituted with deuterium; a biphenylene group unsubstituted or substituted with deuterium; or a naphthylene group unsubstituted or substituted with deuterium.

In one embodiment of the present specification, L1 is a direct bond.

In one embodiment of the present specification, R3 is hydrogen; deuterium; a substituted or unsubstituted C1-C10 alkyl group; a substituted or unsubstituted C3-C30 cycloalkyl group; a substituted or unsubstituted C6-C30 aryl group; or a substituted or unsubstituted C2-C30 heteroaryl group.

In one embodiment of the present specification, R3 is hydrogen; deuterium; a substituted or unsubstituted C1-C6 alkyl group; a substituted or unsubstituted C3-C20 cycloalkyl group; a substituted or unsubstituted C6-C20 aryl group; or a substituted or unsubstituted C2-C20 heteroaryl group.

In one embodiment of the present specification, four or more of R3s are deuterium.

In one embodiment of the present specification, R3 is deuterium.

In one embodiment of the present specification, one of the plurality of R3s is a substituted or unsubstituted aryl group, and specifically, a substituted or unsubstituted C6-C30 aryl group.

In one embodiment of the present specification Chemical Formula 3 is of Chemical Formula 3-1 or 3-2.

[Chemical Formula 3-1]

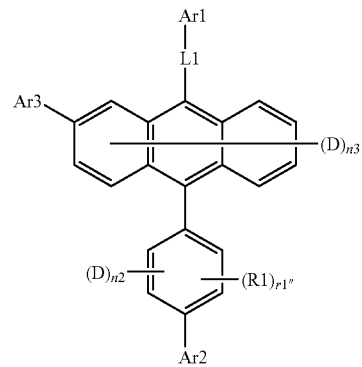

[Chemical Formula 3-2]

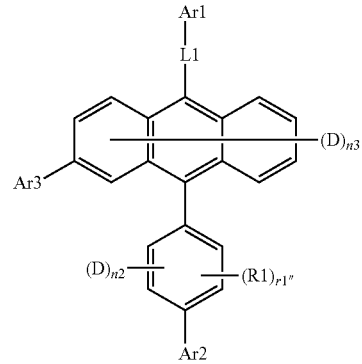

In Chemical Formulae 3-1 and 3-2,

Ar1, Ar2, L1, D, n2, R1, and r1" have the same definitions as in Chemical Formula 3, Ar3 is a substituted or unsubstituted aryl group; or a substituted or unsubstituted heteroaryl group, and n3 is an integer of 0 to 7.

In one embodiment of the present specification, Ar3 is a substituted or unsubstituted C6-C60 aryl group; or a substituted or unsubstituted C2-C60 heteroaryl group.

In one embodiment of the present specification, Ar3 is a substituted or unsubstituted C6-C30 aryl group; or a substituted or unsubstituted C2-C30 heteroaryl group.

In one embodiment of the present specification, Ar3 is a substituted or unsubstituted C6-C20 aryl group; or a substituted or unsubstituted C2-C30 heteroaryl group.

In one embodiment of the present specification, Ar3 is a substituted or unsubstituted phenyl group; a substituted or unsubstituted biphenyl group; a substituted or unsubstituted terphenyl group; a substituted or unsubstituted naphthyl group; a substituted or unsubstituted phenanthrenyl group; a substituted or unsubstituted anthracenyl group; a substituted or unsubstituted triphenylene group; a substituted or unsubstituted fluoranthenyl group; a substituted or unsubstituted phenalene group; a substituted or unsubstituted fluorenyl group; a substituted or unsubstituted benzofluorenyl group; a substituted or unsubstituted spirobifluorenyl group; a substituted or unsubstituted furan group; a substituted or unsubstituted thiophene group; a substituted or unsubstituted dibenzofuran group; a substituted or unsubstituted dibenzothiophene group; a substituted or unsubstituted naphthobenzofuran group; or a substituted or unsubstituted naphthobenzothiophene group.

In one embodiment of the present specification, Ar3 is a C6-C30 aryl group unsubstituted or substituted with deuterium, a C1-C10 alkyl group, a C1-C10 alkyl group substituted with deuterium, a C6-C30 aryl group, or a C6-C30 aryl group substituted with deuterium; or a C2-C30 heteroaryl group unsubstituted or substituted with deuterium, a C6-C30 aryl group, or a C6-C30 aryl group substituted with deuterium.

In one embodiment of the present specification, Ar3 is a phenyl group; a biphenyl group; a 1-naphthyl group; a 2-naphthyl group; a terphenyl group; a phenanthrenyl group; an anthracenyl group; a triphenylene group; a dibenzofuran group; a phenyl-dibenzofuran group; a dibenzothiophene group; a naphthobenzofuran group; a tolyl group; or a xylyl group, and the substituents of Ar3 are unsubstituted or substituted with deuterium.

In one embodiment of the present specification, Ar3 is a phenyl group; a biphenyl group; a 1-naphthyl group; or a 2-naphthyl group, and the substituents of Ar3 are unsubstituted or substituted with deuterium.

In one embodiment of the present specification, n3 is 4 or greater.

In one embodiment of the present specification, n1 is 5, n2 is 4, and r1' and r1" are 0.

In one embodiment of the present specification, Chemical Formula 3 is any one selected from among the following compounds.

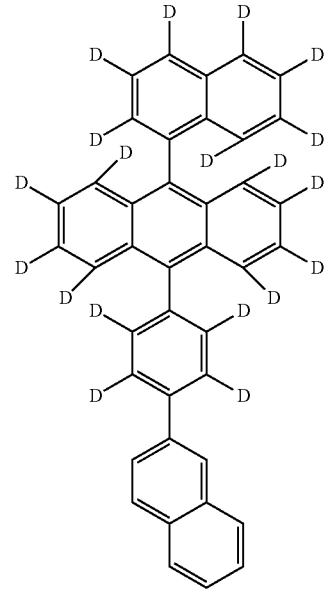

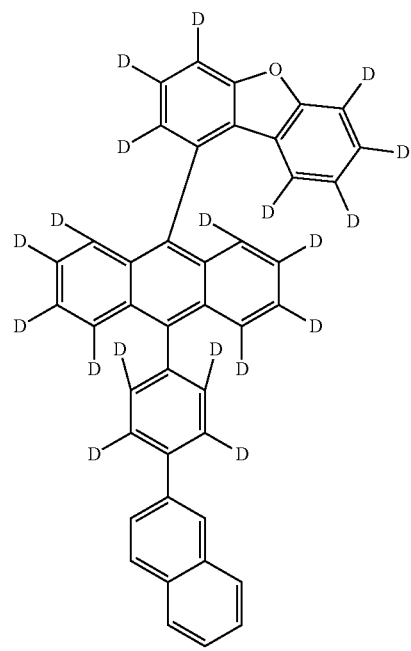

-continued
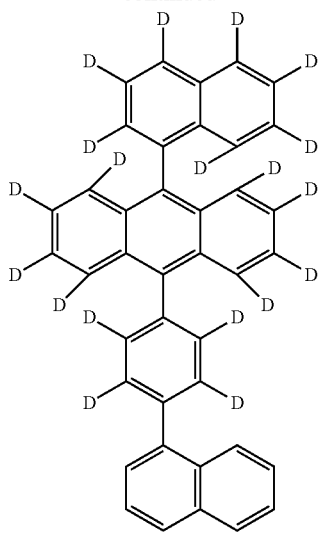
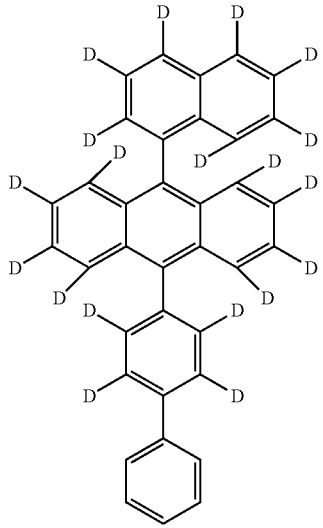
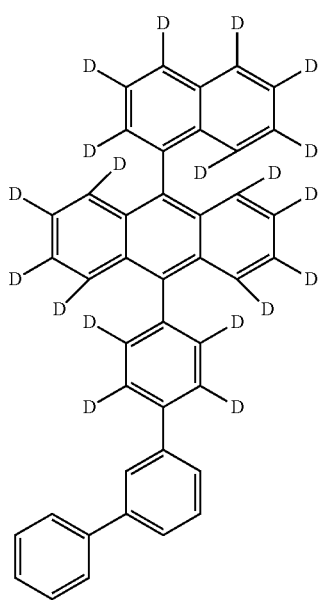
-continued
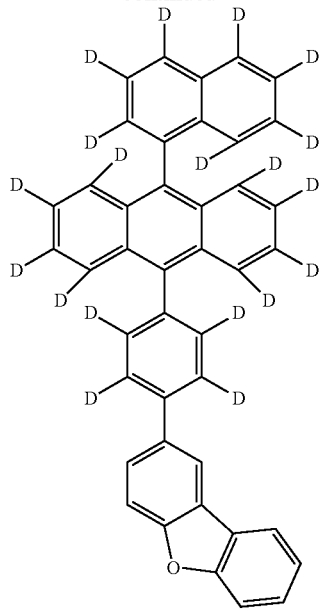
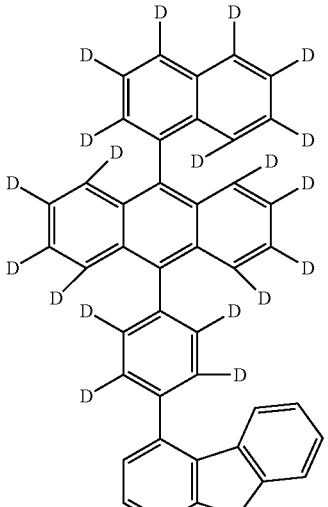
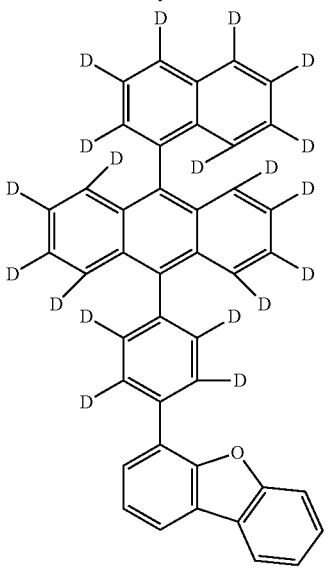

One embodiment of the present specification provides a compound of Chemical Formula 3 prepared using the preparation method.

In addition, one embodiment of the present specification provides a composition including Compound H1 of Chemical Formula 3 having n2 of 4; and Compound H2 of Chemical Formula 3 having n2 of 2 or less, wherein a mass ratio of Compound H1 to Compound H2 is 7:3 to 99.9:0.1.

[Chemical Formula 3]

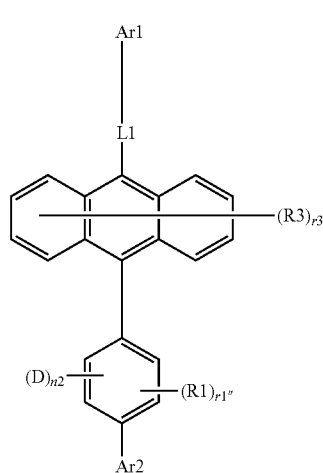

In Chemical Formula 3,

R1 is hydrogen; a cyano group; a nitro group; a halogen group; a hydroxyl group; a substituted or unsubstituted alkyl group; a substituted or unsubstituted cycloalkyl group; a substituted or unsubstituted aryl group; or a substituted or unsubstituted heteroaryl group, R3 is hydrogen; deuterium; a substituted or unsubstituted alkyl group; a substituted or unsubstituted cycloalkyl group; a substituted or unsubstituted aryl group; or a substituted or unsubstituted heteroaryl group, Ar1 and Ar2 are the same as or different from each other, and each independently a substituted or unsubstituted aryl group; or a substituted or unsubstituted heteroaryl group, L1 is a direct bond; a substituted or unsubstituted arylene group; or a substituted or unsubstituted heteroarylene group, D is deuterium, r1″ is an integer of 0 to 3, and when r1″ is 2 or greater, R1s are the same as or different from each other, r3 is an integer of 0 to 8, and when r3 is 2 or greater, R3s are the same as or different from each other, and n2 is an integer of 1 to 4.

Herein, Ar1, L1, R3, r3 and Ar2 of Compounds H1 and H2 are the same as each other. In other words, all the substituents other than n2, R1 and r1″ are the same. Compounds H1 and H2 have the same skeleton and structure, and only the deuterium substitution rate is different.

According to one embodiment of the present specification, n2 is 4 and r1″ is 0 in Compound H1.

In one embodiment of the present specification, n2 is 1 or 2 and r″ is 3 or 2 in Compound H2.

According to one embodiment of the present specification, the composition may be in a solid or liquid state.

According to one embodiment of the present specification, the composition is in a solid state at room temperature and normal pressure.

The composition obtained using the preparation method according to one embodiment of the present specification includes the compound of Chemical Formula 3. Herein, a compound having the same skeleton but having a different deuterium substitution rate is included. A compound having a low deuterium substitution rate of the phenylene group positioned between the anthracene and Ar2 may be included as an impurity.

The composition prepared using the preparation method according to one embodiment of the present specification may have the compound having a high deuterium substitution rate (n2=4) of the phenylene group positioned between the anthracene and Ar2 obtained in a high yield.

In one embodiment of the present specification, Compound H1 and Compound H2 have a mass ratio of 7:3 to 99.9:0.1. More preferably, Compound H1 and Compound H2 have a mass ratio of 8:2 to 99:1.

One embodiment of the present specification provides an organic light emitting device including the compound of Chemical Formula 3 prepared using the preparation method.

Hereinafter, the present specification will be described in detail with reference to examples, comparative examples and the like in order to specifically describe the present specification. However, the examples and the comparative examples according to the present specification may be modified to various different forms, and the scope of the present specification is not to be construed as being limited to the examples and the comparative examples described below. The examples and the comparative examples of the present specification are provided in order to more fully describe to the present specification to those having average knowledge in the art.

Preparation Example 1

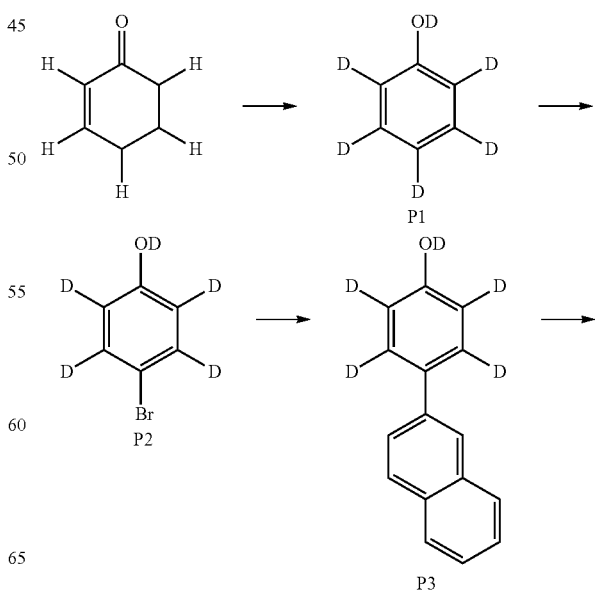

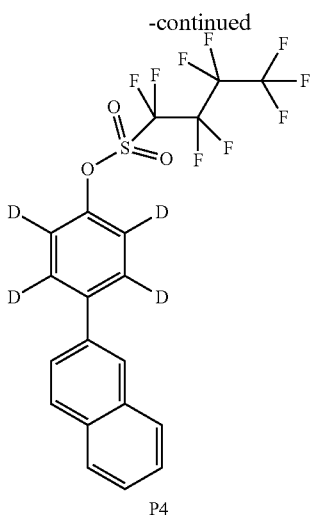

P4

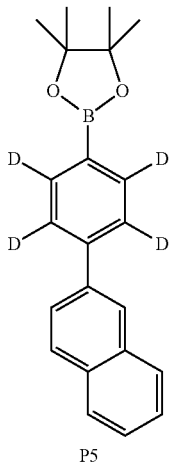

P5

1) Cyclohexen-2-one (518 g, 5.4 mol) was introduced to $D_2O$ (1 L, 55.5 mol), and stirred at room temperature (RT). Iron powder (45 g, 8.1 mol) and 10 wt % Pd/C (28 g, 0.14 mmol) were further introduced thereto, and $N_2$ purge was conducted for 5 minutes. After the introduction, the temperature was raised to 100° C., and the reaction was monitored by HPLC. When the reaction was finished, the result was cooled, and extracted with $Et_2O$. The organic layer was filtered using a silica pad after removing moisture with $MgSO_4$. The filtered organic solution was distilled to obtain phen-2,3,4,5,6-d5-ol-d (280 g, yield 52%).

2) p-TsOH (240 g, 1.4 mol) was introduced to phen-2,3,4,5,6-d5-ol-d (280 g, 2.8 mol), and after 5 minutes, N-bromosuccinimide (495.6 g, 2.8 mol) was introduced thereto. After stirring for 2 hours, the reaction solution was quenched using an aqueous 10% $Na_2S_2O_3$ solution (2 L). After that, the result was extracted using $Et_2O$ (6 L), and moisture was removed from the organic layer using $MgSO_4$. The organic solution was filtered using a silica pad, and the filtrate was purified through column chromatography to obtain 4-bromophen-2,3,5,6-d4-ol-d (225 g, yield 80%).

3) 4-Bromophen-2,3,5,6-d4-ol-d (225 g, 1.3 mol) and 2-naphthylboronic acid (201 g, 1.17 mol) were dissolved in tetrahydrofuran (2.5 L), and an aqueous 30% $K_2CO_3$ solution (1 L) was introduced thereto. The reaction solution was refluxed after raising the temperature, aged for 30 minutes, and then $Pd(dppf)Cl_2$ (9.8 g, 0.013 mol) was introduced thereto. The reaction was monitored by HPLC, and after the reaction was finished, the reaction solution was extracted with water. The organic layer was filtered using a silica pad after removing moisture with $MgSO_4$. The filtrate was purified through column chromatography to obtain 4-(naphthalen-2-yl)phen-2,3,5,6-d4-ol-d (248 g, yield 85%).

4) 4-(Naphthalen-2-yl)phen-2,3,5,6-d4-ol-d (248 g, 1.1 mol) and nonafluorobutanesulfonyl fluoride (408 g, 1.65 mol, 1.5 eq.) were dissolved in acetonitrile (2 L), and $K_2CO_3$ (303 g, 2.2 mol) was introduced thereto. After the introduction, the internal temperature was raised to 50° C., and the reaction was monitored by HPLC. After the reaction was finished, ice water (2 L) was introduced thereto, and the result was filtered using a funnel to obtain 4-(naphthalen-2-yl)phenyl-2,3,5,6-d4 1,1,2,2,3,3,4,4,4-nonafluorobutane-1-sulfonate (528 g, 95%).

5) 4-(Naphthalen-2-yl)phenyl-2,3,5,6-d4 1,1,2,2,3,3,4,4,4-nonafluorobutane-1-sulfonate (528 g, 1.045 mol), pinacolato diboron (291 g, 1.15 mol, 1.1 eq.) and KOAc (263 g, 3.135 mol, 3 eq.) were introduced to a reactor, and 1,4-dioxane (5.3 L) was introduced thereto. The temperature was raised until the reaction solution was refluxed, and $Pd(dppf)Cl_2$ (7.95 g, 104 mmol) was introduced thereto. The reaction was monitored by HPLC, and after the reaction was finished, the reaction solution was cooled, and EtOH (5.3 L) and $H_2O$ (10.6 L) were further introduced thereto. Produced solids were filtered using a funnel, and the filtered solids were dissolved in $CHCl_3$ (1 L) and then purified by column chromatography to obtain 4,4,5,5-tetramethyl-2-(4-(naphthalen-2-yl)phenyl-2,3,5,6-d4)-1,3,2-dioxaborolane (296 g, yield 85%).

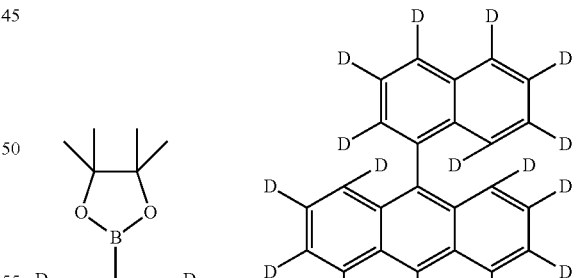

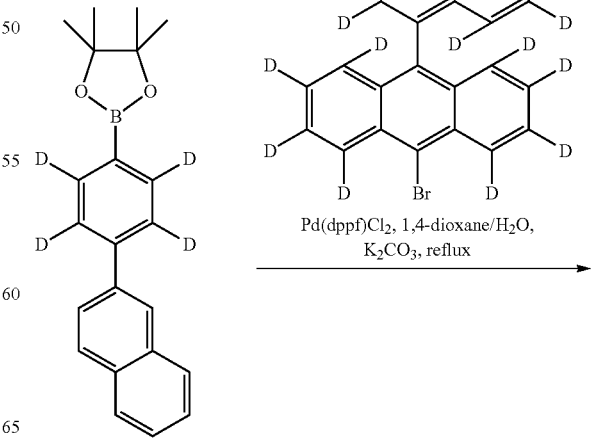

$Pd(dppf)Cl_2$, 1,4-dioxane/$H_2O$, $K_2CO_3$, reflux

-continued

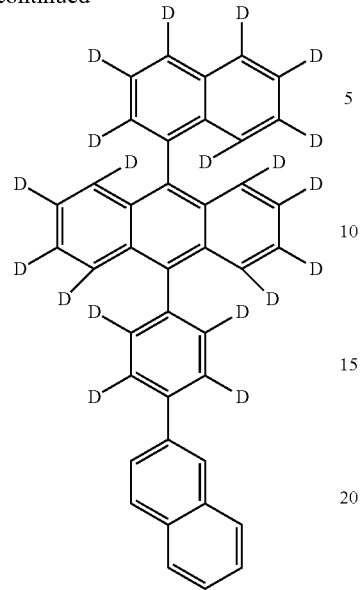

-continued

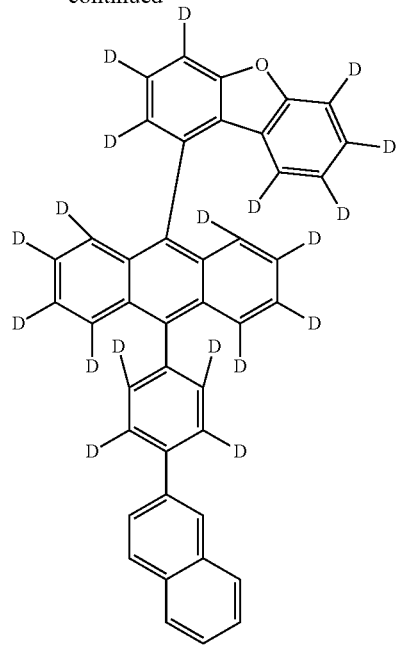

6) 9-Bromo-10-(naphthalen-1-yl)anthracene d15 (100 g, 0.251 mol), 4,4,5,5-tetramethyl-2-(4-(naphthalen-2-yl)phenyl-2,3,5,6-d4)-1,3,2-dioxaborolane (100.69 g, 0.301 mol), potassium carbonate (69 g, 0.502 mol), 1,4-dioxane (1000 L) and water (333 mL) were introduced. The mixture was stirred for 20 minutes at room temperature, then Pd(dppf)Cl$_2$ (0.39 g, 0.5 mmol) was introduced thereto, and the result was refluxed for 5 hours. After that, the reaction mixture was cooled to room temperature, and stirred for 30 minutes. Produced solids were washed with 1,4-dioxane, water and methanol, and then recrystallized with toluene to obtain 9-(naphthalen-1-yl-d7)-10-(4-(naphthalen-2-yl)phenyl-2,3,5,6-d4)anthracene-1,2,3,4,5,6,7,8-d8 (96 g, 72%, deuterium conversion 73%).

Preparation Example 2

1-(10-Bromoanthracen-9-yl-1,2,3,4,5,6,7,8-d8)dibenzo[b,d]furan-2,3,4,6,7,8,9-d7 (109 g, 0.251 mol), 4,4,5,5-tetramethyl-2-(4-(naphthalen-2-yl)phenyl-2,3,5,6-d4)-1,3,2-dioxaborolane (100.66 g, 0.301 mol), potassium carbonate (69 g, 0.502 mol), 1,4-dioxane (1000 L) and water (333 mL) were introduced. The mixture was stirred for 20 minutes at room temperature, then Pd(dppf)Cl$_2$ (0.39 g, 0.5 mmol) was introduced thereto, and the result was refluxed for 5 hours. After that, the reaction mixture was cooled to room temperature, and stirred for 30 minutes. Produced solids were washed with 1,4-dioxane, water and methanol, and then recrystallized with toluene to obtain 1-(10-(4-(naphthalen-2-yl)phenyl-2,3,5,6-d4)anthracen-9-yl-1,2,3,4,5,6,7,8-d8)dibenzo[b,d]furan-2,3,4,6,7,8,9-d7 (113 g, 80%, deuterium conversion 73%).

Various intermediate compounds may be synthesized using different organic boronic acid compounds instead of 2-naphthylboronic acid in 3) of Preparation Example 1.

Preparation Example 3

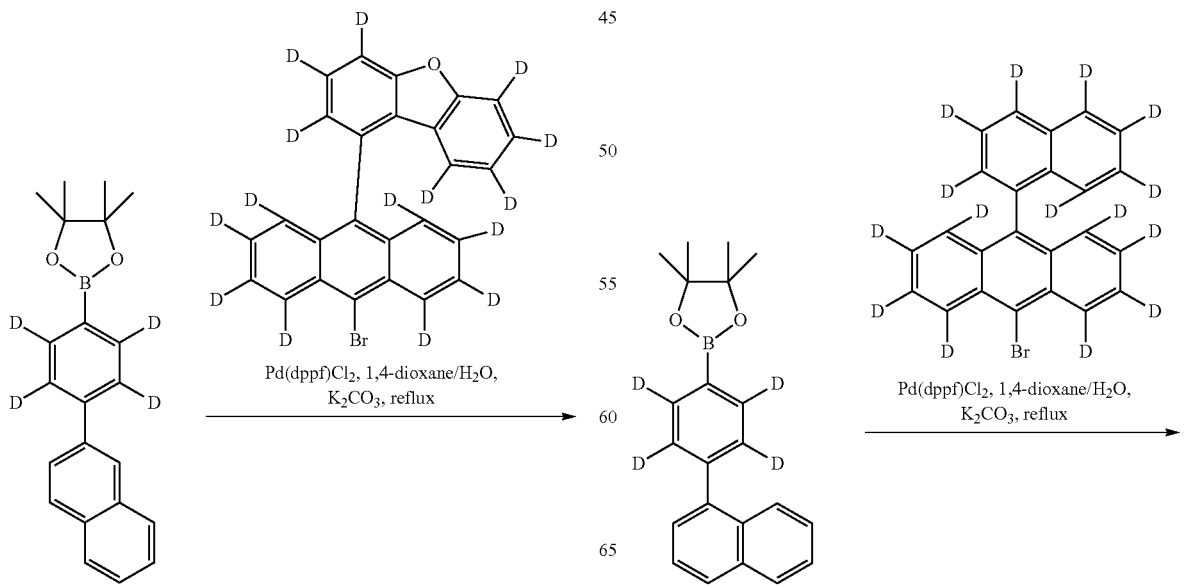

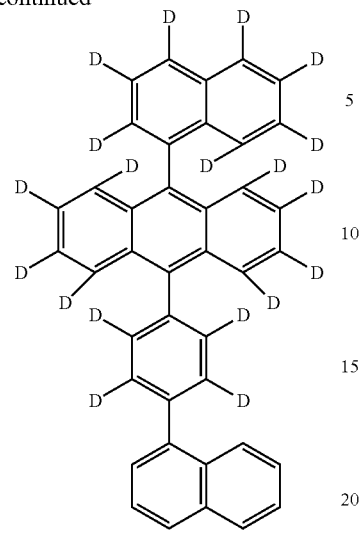

9-Bromo-10-(naphthalen-1-yl)anthracene d15 (100 g, 0.251 mol), 4,4,5,5-tetramethyl-2-(4-(naphthalen-1-yl)phenyl-2,3,5,6-d4)-1,3,2-dioxaborolane (100.69 g, 0.301 mol), potassium carbonate (69 g, 0.502 mol), 1,4-dioxane (1000 L) and water (333 mL) were introduced. The mixture was stirred for 20 minutes at room temperature, then Pd(dppf)Cl$_2$ (0.39 g, 0.5 mmol) was introduced thereto, and the result was refluxed for 5 hours. After that, the reaction mixture was cooled to room temperature, and stirred for 30 minutes. Produced solids were washed with 1,4-dioxane, water and methanol, and then recrystallized with toluene to obtain 9-(naphthalen-1-yl-d7)-10-(4-(naphthalen-1-yl)phenyl-2,3,5,6-d4)anthracene-1,2,3,4,5,6,7,8-d8 (89.6 g, 68%, deuterium conversion 73%).

Preparation Example 4

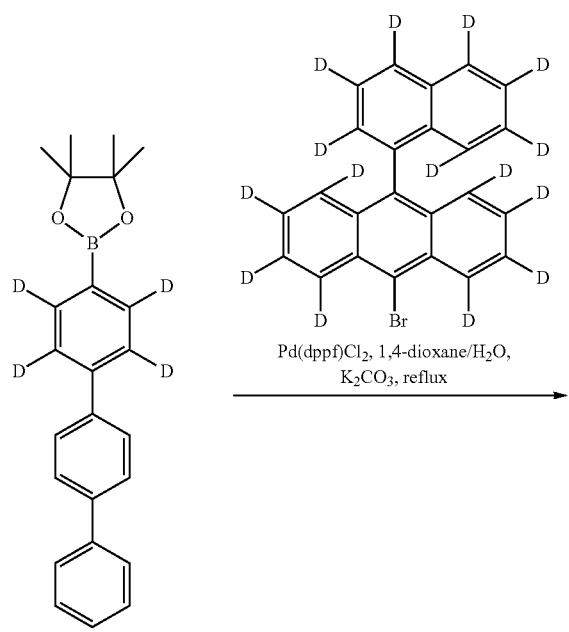

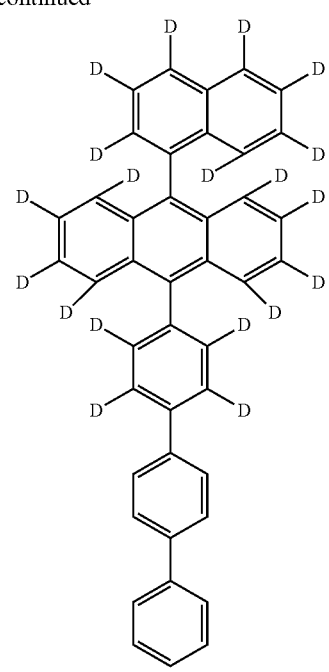

9-Bromo-10-(naphthalen-1-yl)anthracene d15 (100 g, 0.251 mol), 2-([1,1':4',1"-terphenyl]-4-yl-2,3,5,6-d4)-4,4,5,5-tetramethyl-1,3,2-dioxaborolane (108.36 g, 0.301 mol), potassium carbonate (69 g, 0.502 mol), 1,4-dioxane (1000 L) and water (333 mL) were introduced. The mixture was stirred for 20 minutes at room temperature, then Pd(dppf)Cl$_2$ (0.39 g, 0.5 mmol) was introduced thereto, and the result was refluxed for 5 hours. After that, the reaction mixture was cooled to room temperature, and stirred for 30 minutes. Produced solids were washed with 1,4-dioxane, water and methanol, and then recrystallized with toluene to obtain 9-([1,1':4',1"-terphenyl]-4-yl-2,3,5,6-d4)-10-(naphthalen-1-yl-d7)anthracene-1,2,3,4,5,6,7,8-d8 (117 g, 85%, deuterium conversion 68%).

Preparation Example 5

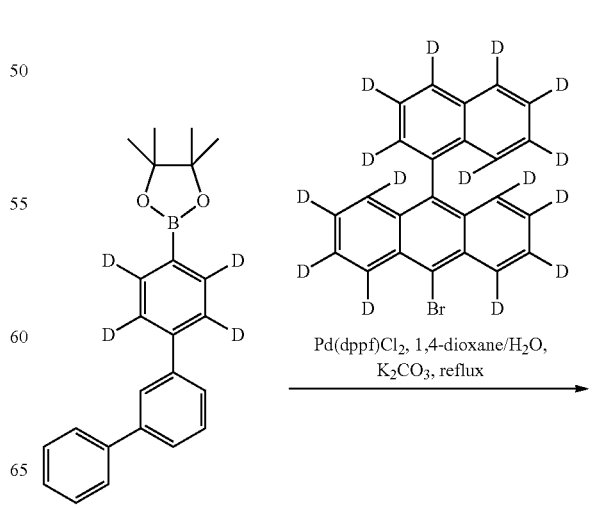

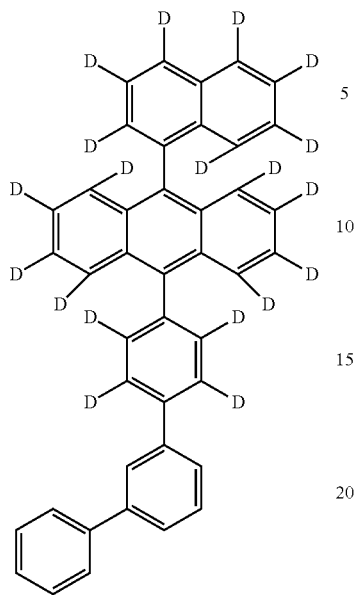

9-Bromo-10-(naphthalen-1-yl)anthracene d15 (100 g, 0.251 mol), 2-([1,1':3',1"-terphenyl]-4-yl-2,3,5,6-d4)-4,4,5,5-tetramethyl-1,3,2-dioxaborolane (108.36 g, 0.301 mol), potassium carbonate (69 g, 0.502 mol), 1,4-dioxane (1000 L) and water (333 mL) were introduced. The mixture was stirred for 20 minutes at room temperature, then Pd(dppf)Cl$_2$ (0.39 g, 0.5 mmol) was introduced thereto, and the result was refluxed for 5 hours. After that, the reaction mixture was cooled to room temperature, and stirred for 30 minutes. Produced solids were washed with 1,4-dioxane, water and methanol, and then recrystallized with toluene to obtain 9-([1,1':3',1"-terphenyl]-4-yl-2,3,5,6-d4)-10-(naphthalen-1-yl-d7)anthracene-1,2,3,4,5,6,7,8-d8 (113.4 g, 82%, deuterium conversion 68%).

9-Bromo-10-(naphthalen-1-yl)anthracene d15 (100 g, 0.251 mol), 2-(4-(dibenzo[b,d]furan-2-yl)phenyl-2,3,5,6-d4)-4,4,5,5-tetramethyl-1,3,2-dioxaborolane (112.63 g, 0.301 mol), potassium carbonate (69 g, 0.502 mol), 1,4-dioxane (1000 L) and water (333 mL) were introduced. The mixture was stirred for 20 minutes at room temperature, then Pd(dppf)Cl$_2$ (0.39 g, 0.5 mmol) was introduced thereto, and the result was refluxed for 5 hours. After that, the reaction mixture was cooled to room temperature, and stirred for 30 minutes. Produced solids were washed with 1,4-dioxane, water and methanol, and then recrystallized with toluene to obtain 2-(4-(10-(naphthalen-1-yl-d7)anthracen-9-yl-1,2,3,4,5,6,7,8-d8)phenyl-2,3,5,6-d4)dibenzo[b,d]furan (106.36 g, 75%, deuterium conversion 73%).

Preparation Example 6

Preparation Example 7

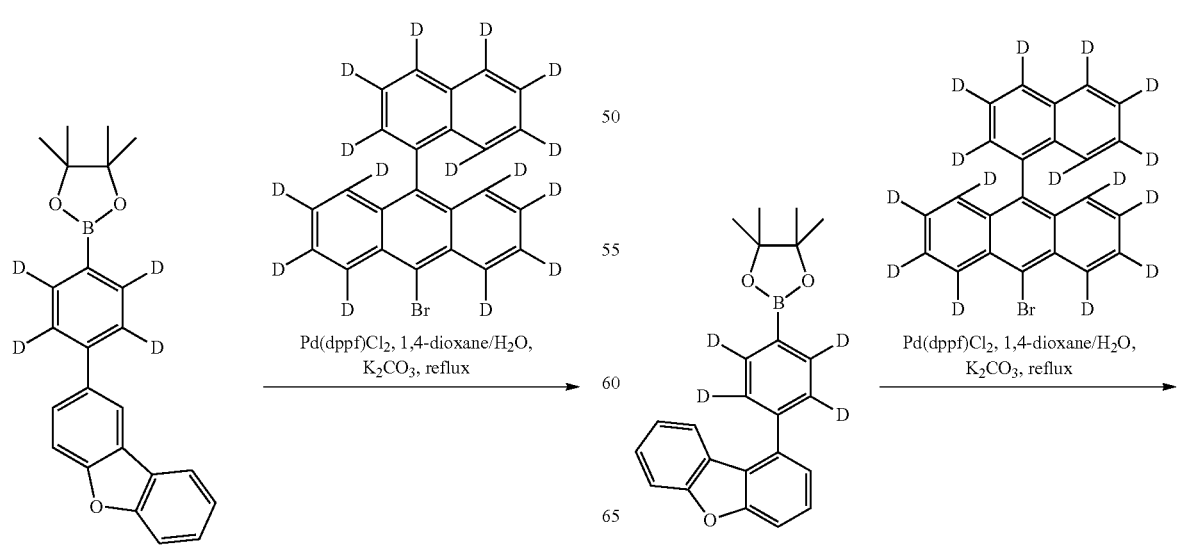

27
-continued

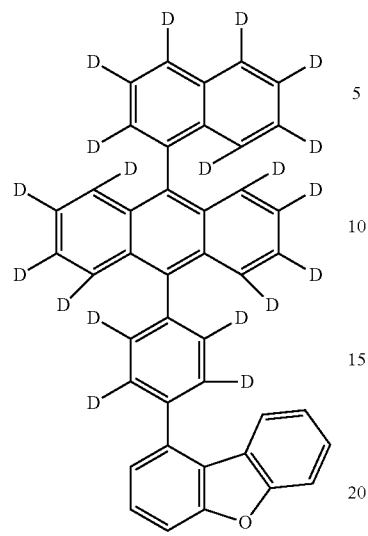

9-Bromo-10-(naphthalen-1-yl)anthracene d15 (100 g, 0.251 mol), 2-(4-(dibenzo[b,d]furan-1-yl)phenyl-2,3,5,6-d4)-4,4,5,5-tetramethyl-1,3,2-dioxaborolane (112.63 g, 0.301 mol), potassium carbonate (69 g, 0.502 mol), 1,4-dioxane (1000 L) and water (333 mL) were introduced. The mixture was stirred for 20 minutes at room temperature, then Pd(dppf)Cl$_2$ (0.39 g, 0.5 mmol) was introduced thereto, and the result was refluxed for 5 hours. After that, the reaction mixture was cooled to room temperature, and stirred for 30 minutes. Produced solids were washed with 1,4-dioxane, water and methanol, and then recrystallized with toluene to obtain 1-(4-(10-(naphthalen-1-yl-d7)anthracen-9-yl-1,2,3,4, 5,6,7,8-d8)phenyl-2,3,5,6-d4)dibenzo[b,d]furan (99.27 g, 70%, deuterium conversion 73%).

Preparation Example 8

28
-continued

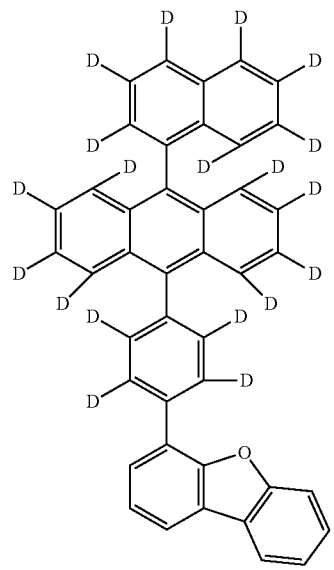

9-Bromo-10-(naphthalen-1-yl)anthracene d15 (100 g, 0.251 mol), 2-(4-(dibenzo[b,d]furan-4-yl)phenyl-2,3,5,6-d4)-4,4,5,5-tetramethyl-1,3,2-dioxaborolane (112.63 g, 0.301 mol), potassium carbonate (69 g, 0.502 mol), 1,4-dioxane (1000 L) and water (333 mL) were introduced. The mixture was stirred for 20 minutes at room temperature, then Pd(dppf)Cl$_2$ (0.39 g, 0.5 mmol) was introduced thereto, and the result was refluxed for 5 hours. After that, the reaction mixture was cooled to room temperature, and stirred for 30 minutes. Produced solids were washed with 1,4-dioxane, water and methanol, and then recrystallized with toluene to obtain 4-(4-(10-(naphthalen-1-yl-d7)anthracen-9-yl-1,2,3,4, 5,6,7,8-d8)phenyl-2,3,5,6-d4)dibenzo[b,d]furan (92.17 g, 65%, deuterium conversion 73%).

Comparative Example 1

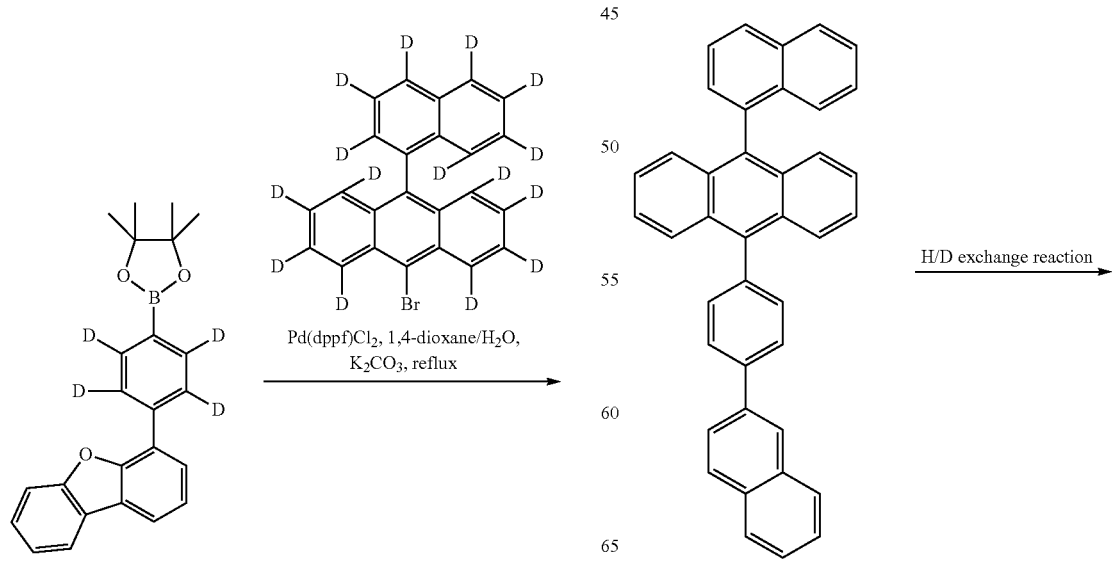

-continued

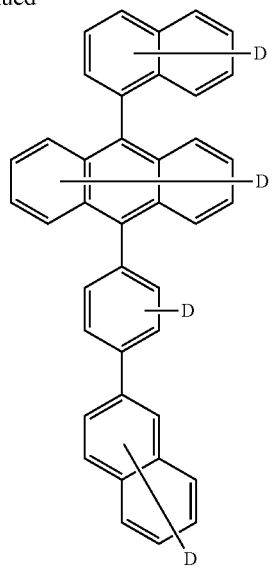

1) 9-(Naphthalen-1-yl)anthracene (100 g, 0.329 mol) was introduced and dissolved in a D6-benzene solution (500 ml, 475 g, 5.645 mol) (D substitution reaction condition: $C_6D_6$ 7v (ml/g)). After raising the temperature of the solution to 80° C., triflic acid (10 mL, 0.113 mol) was slowly added dropwise to the solution. The result was stirred for 40 minutes, and, after checking the substitution rate, quenched with $D_2O$ (40 ml, 1.997 mol). After the reaction was finished, the reaction solution was layer-separated, and, after removing moisture of the organic solution with $MgSO_4$, acidic clay was added thereto and stirred. The solution was filtered using a silica pad, and the solvent was removed by rotary distillation. As a result, 9-(naphthalen-1-yl)anthracene crude oil (85 g, yield 81%) was obtained.

2) DMF (250 ml, 3.229 mol) was introduced to the crude oil (85 g, 0.265 mol) for dissolution, and N-bromosuccinimide (141.6 g, 0.329 mol) was added thereto. After the reaction was finished, EtOH (200 ml, 3.43 mol) was introduced thereto, and the result was quenched by adding 10% sodium metabisulfite aq. (1.2 L) thereto. Produced solids were filtered to obtain crude solids (87.8 g, 0.226 mol, 67%).

3) 1-(10-Bromoanthracen-9-yl-1,2,3,4,5,6,7,8-d8)dibenzo[b,d]furan-2,3,4,6,7,8,9-d7 (109 g, 0.251 mol), 4,4,5,5-tetramethyl-2-(4-(naphthalen-2-yl)phenyl-2,3,5,6-d4)-1,3,2-dioxaborolane (100.66 g, 0.301 mol), potassium carbonate (69 g, 0.502 mol), 1,4-dioxane (1000 L) and water (333 mL) were introduced. The mixture was stirred for 20 minutes at room temperature, then $Pd(dppf)Cl_2$ (0.39 g, 0.5 mmol) was introduced thereto, and the result was refluxed for 5 hours. After that, the reaction mixture was cooled to room temperature, and stirred for 30 minutes. Produced solids were washed with 1,4-dioxane, water and methanol, and then recrystallized with toluene to obtain 1-(10-(4-(naphthalen-2-yl)phenyl-2,3,5,6-d4)anthracen-9-yl-1,2,3,4,5,6,7,8-d8)dibenzo[b,d]furan-2,3,4,6,7,8,9-d7 (113 g, 80%).

Comparative Examples 2 and 3

The following compounds were prepared in the same manner as in Comparative Example 1 except that the D substitution reaction condition was changed as follows.
Comparative Example 2: $C_6D_6$ 12v (ml/g)
Comparative Example 3: $C_6D_6$ 17v (ml/g)

Evaluation Example

The deuterium substituents of the 9-(naphthalen-1-yl)-10-(4-(naphthalen-2-yl)phenyl)anthracene, and 9-(naphthalen-1-yl)-10-(4-(naphthalen-2-yl)phenyl)anthracene not substituted with deuterium prepared in Preparation Example 1 and Comparative Examples 1 to 3 were analyzed by NMR under the following condition.

NMR device: Bruker 700 MHz NMR
Select corresponding probe: Probe (PABBO)
D-solvent: (THF-d8)
Experiment temperature: 298K
Parameter set up follows SOP procedure.

FIG. 1 is an NMR spectrum of the 9-(naphthalen-1-yl)-10-(4-(naphthalen-2-yl)phenyl)anthracene not substituted with deuterium.

Figure 2:
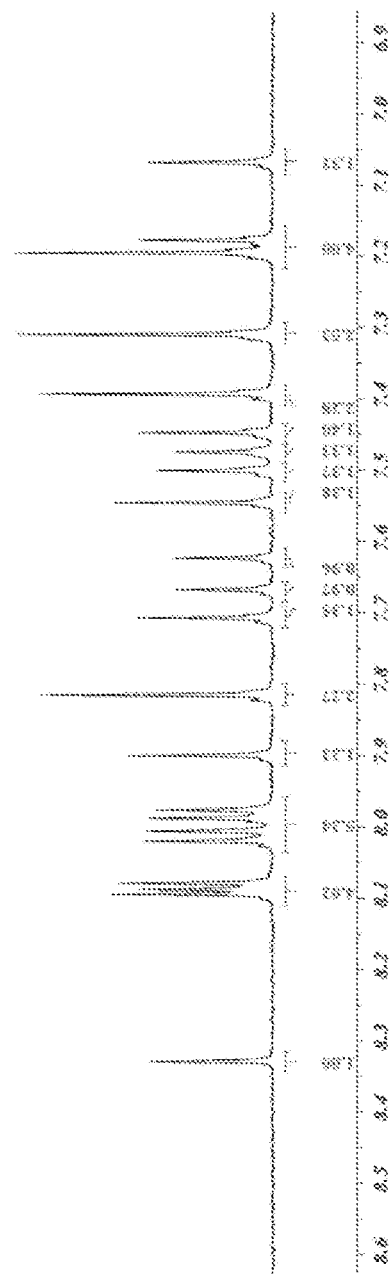
FIG. 2 is an NMR spectrum of a deuterium substituent of 9-(naphthalen-1-yl)-10-(4-(naphthalen-2-yl)phenyl)anthracene prepared in Preparation Example 1 of the present disclosure.

FIG. 2 is an NMR spectrum of the deuterium substituent of the 9-(naphthalen-1-yl)-10-(4-(naphthalen-2-yl)phenyl)anthracene prepared in Preparation Example 1 of the present disclosure.

Figure 3:
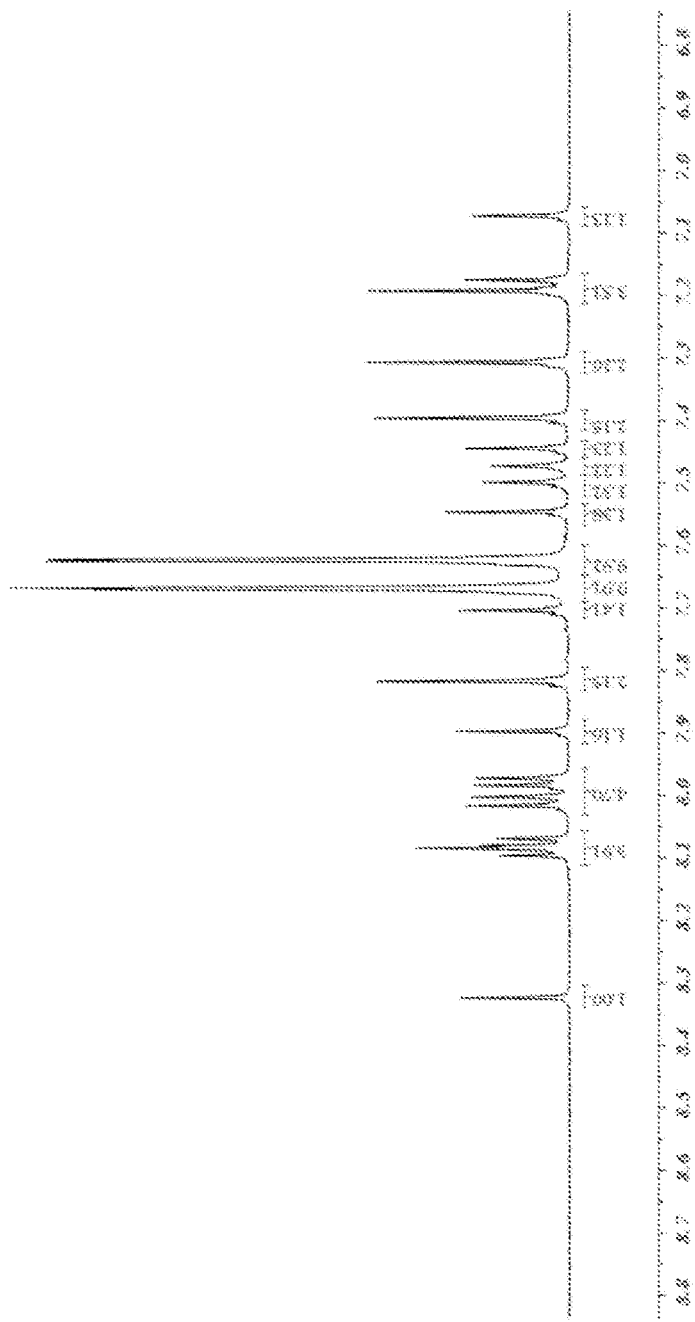
FIG. 3 is an NMR spectrum of a deuterium substituent of 9-(naphthalen-1-yl)-10-(4-(naphthalen-2-yl)phenyl)anthracene prepared in Comparative Example 1.

FIG. 3 is an NMR spectrum of the deuterium substituent of the 9-(naphthalen-1-yl)-10-(4-(naphthalen-2-yl)phenyl)anthracene prepared in Comparative Example 1.

Figure 4:
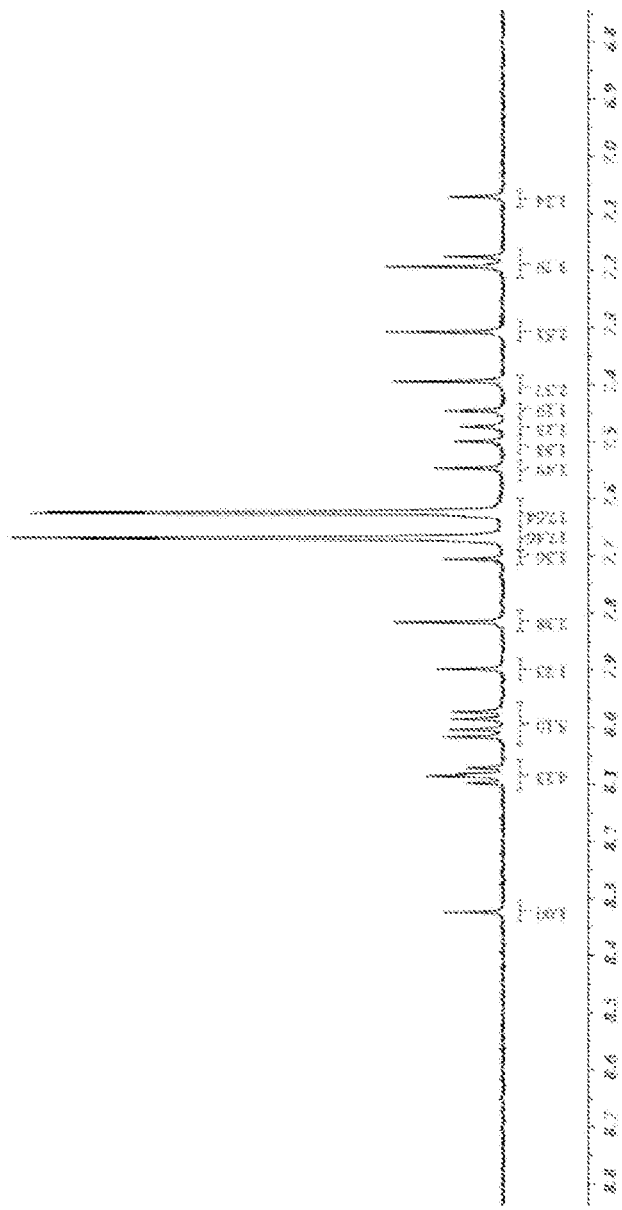
FIG. 4 is an NMR spectrum of a deuterium substituent of 9-(naphthalen-1-yl)-10-(4-(naphthalen-2-yl)phenyl)anthracene prepared in Comparative Example 2.

FIG. 4 is an NMR spectrum of the deuterium substituent of the 9-(naphthalen-1-yl)-10-(4-(naphthalen-2-yl)phenyl)anthracene prepared in Comparative Example 2.

Figure 5:
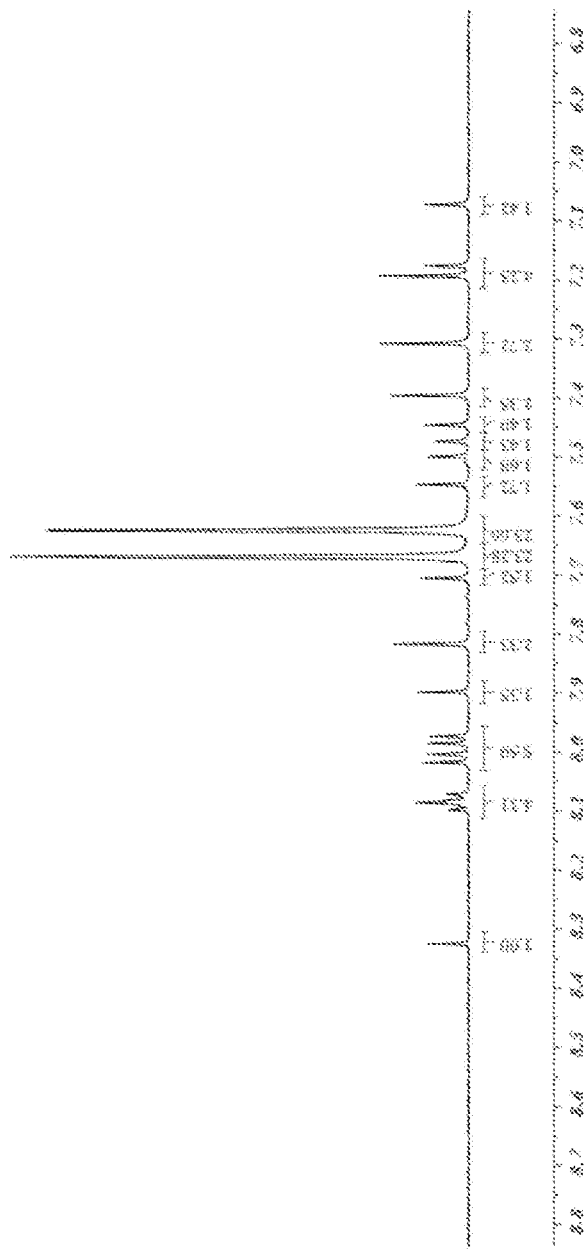
FIG. 5 is an NMR spectrum of a deuterium substituent of 9-(naphthalen-1-yl)-10-(4-(naphthalen-2-yl)phenyl)anthracene prepared in Comparative Example 3.

FIG. 5 is an NMR spectrum of the deuterium substituent of the 9-(naphthalen-1-yl)-10-(4-(naphthalen-2-yl)phenyl)anthracene prepared in Comparative Example 3.

Based on the 9-(naphthalen-1-yl)-10-(4-(naphthalen-2-yl)phenyl)anthracene not substituted with deuterium, NMR spectra of the deuterium substituents prepared in Preparation Example 1 and Comparative Examples 1 to 3 were analyzed, and the deuterium substitution rate at each position was calculated using a peak integration value ratio for each hydrogen (proton) position (decreased as much as deuterium substitution). Among these, the deuterium substitution rates at positions close to the anthracene, that is, Nos. 2 and 3 of the following phenyl group B are shown in the following Table 1.

9-(naphthalen-1-yl)-10-(4-(naphthalen-2-yl)phenyl)anthracene

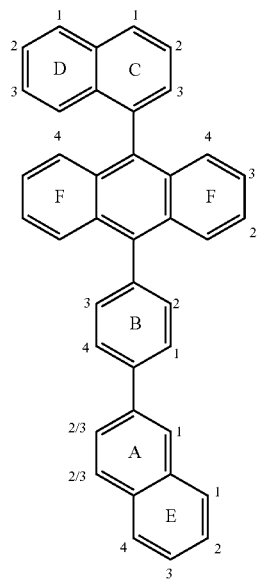

TABLE 1

| Position | Example 1 | | Comparative Example 1 | | Comparative Example 2 | | Comparative Example 3 | |
|---|---|---|---|---|---|---|---|---|
| | B2 | B3 | B2 | B3 | B2 | B3 | B2 | B3 |
| Number of H | 1 | 1 | 1 | 1 | 1 | 1 | 1 | 1 |
| D Substitution Rate (%) | 91.0 | 91.1 | 3 | 3 | 4 | 3 | 19 | 18 |

As identified in Table 1 and FIG. 2 to FIG. 5, it was seen that the deuterium substituent prepared according to the preparation method of the present disclosure had a very high deuterium substitution rate at a sterically unfree site (B2 and B3). On the other hand, the deuterium substitution rate at a sterically unfree site (B2 and B3) was very low when the undeuterated compound was deuterated by treating with a deuterated solvent (Comparative Examples 1 to 3).

In addition, it was seen that the preparation method of the present disclosure used a smaller amount of deuterium with respect to the deuterium substitution rate.

The invention claimed is:

1. A method for preparing a deuterated compound, the method comprising:
   preparing a compound of Chemical Formula 2 by reacting a compound of Chemical Formula 1; a deuterium source; and a metal catalyst, and
   forming a compound of Chemical Formula 3 reacting the compound of Chemical Formula 2,

[Chemical Formula 1]

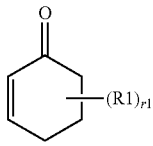

[Chemical Formula 2]

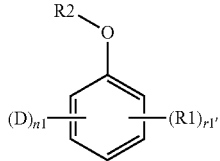

[Chemical Formula 3]

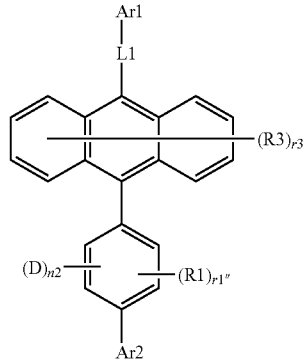

wherein in Chemical Formulae 1 to 3,
R1 is hydrogen; a cyano group; a nitro group; a halogen group; a hydroxyl group; a substituted or unsubstituted alkyl group; a substituted or unsubstituted cycloalkyl group; a substituted or unsubstituted aryl group; or a substituted or unsubstituted heteroaryl group, R2 is hydrogen or deuterium, R3 is hydrogen; deuterium; a substituted or unsubstituted alkyl group; a substituted or unsubstituted cycloalkyl group; a substituted or unsubstituted aryl group; or a substituted or unsubstituted heteroaryl group, Ar1 and Ar2 are the same as or different from each other, and each independently a substituted or unsubstituted aryl group; or a substituted or unsubstituted heteroaryl group, L1 is a direct bond; a substituted or unsubstituted arylene group; or a substituted or unsubstituted heteroarylene group, D is deuterium, r1 is an integer of 0 to 8, r1' is an integer of 0 to 4, r1" is an integer of 0 to 3, and when r1, r1' and r1" are 2 or greater, R1s are the same as or different from each other, r3 is an integer of 0 to 8, and when r3 is 2 or greater, R3s are the same as or different from each other, and n1 is an integer of 1 to 5, and n2 is an integer of 1 to 4.

2. The method of claim 1, wherein n1 is 5, n2 is 4, and r1' and r1" are 0.

3. The method of claim 1, wherein the deuterium source is heavy water ($D_2O$), perdeuterated benzene (benzene-$D_6$), perdeuterated toluene (toluene-$D_8$), perdeuterated xylene (xylene-$D_{10}$), deuterium-hydrochloric acid (DCl), deuterium-sulfuric acid ($D_2SO_4$), deuterium-trifluoroacetic acid ($CF_3COOD$), deuterium-triflic acid ($CF_3SO_3OD$), deuterium-chloroform ($CDCl_3$), perdeuterated methanol ($CD_3OD$), or a mixture of two or more thereof.

4. The method of claim 1, wherein the metal catalyst is platinum, palladium, rhodium, ruthenium, nickel, cobalt, iron, oxides thereof, complexes thereof, or a mixture of two or more thereof.

5. The method of claim 1, wherein the deuterium source in the step of preparing the compound of Chemical Formula 2 is included in 1 equivalent to 50 equivalents with respect to 1 equivalent of the compound of Chemical Formula 1.

6. The method of claim 1, wherein the step of preparing the compound of Chemical Formula 2 is conducted at a temperature of 20° C. or higher.

7. The method of claim 1, wherein the step of preparing the compound of Chemical Formula 2 includes:
   stirring a mixture of the compound of Chemical Formula 1 and the deuterium source;
   mixing the metal catalyst with the mixture and adjusting a temperature; and
   obtaining the compound of Chemical Formula 2.

8. The method of claim 1, wherein the step of forming the compound of Chemical Formula 3 includes:
   halogenating the compound of Chemical Formula 2 to form a halogenated compound;
   substituting halogen of the halogenated compound with Ar2 by reacting the halogenated compound with an organic boron compound containing Ar2 to form a compound including Ar2; and
   reacting the compound including Ar2 and an anthracene derivative to form a carbon-carbon bond therebetween.

* * * * *